(12) United States Patent
Santra et al.

(10) Patent No.: US 11,614,516 B2
(45) Date of Patent: Mar. 28, 2023

(54) RADAR VITAL SIGNAL TRACKING USING A KALMAN FILTER

(71) Applicant: Infineon Technologies AG, Neubiberg (DE)

(72) Inventors: Avik Santra, Munich (DE); Muhammad Arsalan, Munich (DE); Christoph Will, Munich (DE)

(73) Assignee: Infineon Technologies AG, Neubiberg (DE)

( * ) Notice: Subject to any disclaimer, the term of this patent is extended or adjusted under 35 U.S.C. 154(b) by 236 days.

(21) Appl. No.: 16/794,904

(22) Filed: Feb. 19, 2020

(65) Prior Publication Data

US 2021/0255280 A1 Aug. 19, 2021

(51) Int. Cl.
| | | |
|---|---|---|
| *G01S 7/35* | (2006.01) | |
| *G01S 13/72* | (2006.01) | |
| *A61B 5/0507* | (2021.01) | |
| *A61B 5/024* | (2006.01) | |
| *A61B 5/00* | (2006.01) | |

(Continued)

(52) U.S. Cl.
CPC .............. *G01S 7/415* (2013.01); *A61B 5/024* (2013.01); *A61B 5/02405* (2013.01); *A61B 5/0507* (2013.01); *A61B 5/725* (2013.01); *G01S 7/354* (2013.01); *G01S 13/50* (2013.01); *G01S 13/723* (2013.01); *G01S 7/358* (2021.05)

(58) Field of Classification Search
CPC .......... G01S 7/415; G01S 7/354; G01S 13/50; G01S 13/723; G01S 7/358; G01S 13/42; G01S 13/584; G01S 13/88; G01S 13/343; A61B 5/02405; A61B 5/0507; A61B 5/024; A61B 5/72; A61B 5/02444

See application file for complete search history.

(56) References Cited

U.S. PATENT DOCUMENTS 4,241,347 A 12/1980 Albanese et al.
5,687,733 A * 11/1997 McKown ............... A61B 5/028
600/526

(Continued)

FOREIGN PATENT DOCUMENTS

CN 1463161 A 12/2003
CN 1716695 A 1/2006

(Continued)

OTHER PUBLICATIONS https://en.wikipedia.org/wiki/Kalman_filter, accessed on Apr. 1, 2022. (Year: 2020).*

(Continued)

*Primary Examiner* — Donald H B Braswell
(74) *Attorney, Agent, or Firm* — Slater Matsil, LLP

(57) ABSTRACT

In an embodiment, a method includes: receiving reflected radar signals with a millimeter-wave radar; generating a displacement signal indicative of a displacement of a target based on the reflected radar signals; filtering the displacement signal using a bandpass filter to generate a filtered displacement signal; determining a first rate indicative of a heartbeat rate of the target based on the filtered displacement signal; tracking a second rate indicative of the heartbeat rate of the target with a track using a Kalman filter; updating the track based on the first rate; and updating a setting of the bandpass filter based on the updated track.

20 Claims, 5 Drawing Sheets

(51) Int. Cl.
  *G01S 7/41* (2006.01)
  *G01S 13/50* (2006.01)

(56) References Cited

U.S. PATENT DOCUMENTS

| | | | |
|---|---|---|---|
| 6,147,572 A | 11/2000 | Kaminski et al. |
| 6,414,631 B1 | 7/2002 | Fujimoto |
| 6,636,174 B2 | 10/2003 | Arikan et al. |
| 7,048,973 B2 | 5/2006 | Sakamoto et al. |
| 7,057,564 B2 | 6/2006 | Tsai et al. |
| 7,171,052 B2 | 1/2007 | Park |
| 7,317,417 B2 | 1/2008 | Arikan et al. |
| 7,596,241 B2 | 9/2009 | Rittscher et al. |
| 7,692,574 B2 | 4/2010 | Nakagawa |
| 7,873,326 B2 | 1/2011 | Sadr |
| 7,889,147 B2 | 2/2011 | Tam et al. |
| 8,228,382 B2 | 7/2012 | Pattikonda |
| 8,497,805 B2 | 7/2013 | Rofougaran et al. |
| 8,659,369 B2 | 2/2014 | Rofougaran et al. |
| 8,731,502 B2 | 5/2014 | Salle et al. |
| 8,836,596 B2 | 9/2014 | Richards et al. |
| 8,847,814 B2 | 9/2014 | Himmelstoss et al. |
| 8,860,532 B2 | 10/2014 | Gong et al. |
| 8,976,061 B2 | 3/2015 | Chowdhury |
| 9,172,132 B2 | 10/2015 | Kam et al. |
| 9,182,476 B2 | 11/2015 | Wintermantel |
| 9,202,105 B1 | 12/2015 | Wang et al. |
| 9,413,079 B2 | 8/2016 | Kamgaing et al. |
| 9,477,812 B2 | 10/2016 | Lin et al. |
| 9,495,600 B2 | 11/2016 | Heu et al. |
| 9,886,095 B2 | 2/2018 | Pothier |
| 9,935,065 B1 | 4/2018 | Baheti et al. |
| 10,601,630 B1 | 3/2020 | Dickerman et al. |
| 10,795,012 B2 | 10/2020 | Santra et al. |
| 2003/0179127 A1 | 9/2003 | Wienand |
| 2004/0238857 A1 | 12/2004 | Beroz et al. |
| 2006/0001572 A1 | 1/2006 | Gaucher et al. |
| 2006/0049995 A1 | 3/2006 | Imaoka et al. |
| 2006/0067456 A1 | 3/2006 | Ku et al. |
| 2007/0210959 A1 | 9/2007 | Herd et al. |
| 2008/0074307 A1 | 3/2008 | Boric-Lubecke et al. |
| 2008/0077015 A1 | 3/2008 | Boric-Lubecke et al. |
| 2008/0106460 A1 | 5/2008 | Kurtz et al. |
| 2008/0119716 A1 | 5/2008 | Boric-Lubecke et al. |
| 2008/0238759 A1 | 10/2008 | Carocari et al. |
| 2008/0291115 A1 | 11/2008 | Doan et al. |
| 2008/0308917 A1 | 12/2008 | Pressel et al. |
| 2009/0073026 A1 | 3/2009 | Nakagawa |
| 2009/0085815 A1 | 4/2009 | Jakab et al. |
| 2009/0153428 A1 | 6/2009 | Rofougaran et al. |
| 2009/0315761 A1 | 12/2009 | Walter et al. |
| 2010/0152600 A1 | 6/2010 | Droitcour et al. |
| 2010/0207805 A1 | 8/2010 | Haworth |
| 2011/0299433 A1 | 12/2011 | Darabi et al. |
| 2012/0022348 A1 | 1/2012 | Droitcour et al. |
| 2012/0087230 A1 | 4/2012 | Guo et al. |
| 2012/0092284 A1 | 4/2012 | Rofougaran et al. |
| 2012/0116231 A1 | 5/2012 | Liao et al. |
| 2012/0146796 A1* | 6/2012 | Margon ............... A61B 5/05 340/573.1 |
| 2012/0195161 A1 | 8/2012 | Little et al. |
| 2012/0206339 A1 | 8/2012 | Dahl |
| 2012/0265486 A1 | 10/2012 | Klofer et al. |
| 2012/0268314 A1 | 10/2012 | Kuwahara et al. |
| 2012/0280900 A1 | 11/2012 | Wang et al. |
| 2013/0027240 A1 | 1/2013 | Chowdhury |
| 2013/0106673 A1 | 5/2013 | McCormack et al. |
| 2013/0176161 A1* | 7/2013 | Derham ............... G01S 13/04 342/27 |
| 2014/0028542 A1 | 1/2014 | Lovitt et al. |
| 2014/0070994 A1 | 3/2014 | Schmalenberg et al. |
| 2014/0145883 A1 | 5/2014 | Baks et al. |
| 2014/0324888 A1 | 10/2014 | Xie et al. |
| 2015/0181840 A1 | 7/2015 | Tupin, Jr. et al. |
| 2015/0185316 A1 | 7/2015 | Rao et al. |
| 2015/0212198 A1 | 7/2015 | Nishio et al. |
| 2015/0243575 A1 | 8/2015 | Strothmann et al. |
| 2015/0277569 A1 | 10/2015 | Sprenger et al. |
| 2015/0301167 A1* | 10/2015 | Sentelle ............... G01S 13/56 342/22 |
| 2015/0325925 A1 | 11/2015 | Kamgaing et al. |
| 2015/0346820 A1 | 12/2015 | Poupyrev et al. |
| 2015/0348821 A1 | 12/2015 | Iwanaga et al. |
| 2015/0364816 A1 | 12/2015 | Murugan et al. |
| 2016/0018511 A1 | 1/2016 | Nayyar et al. |
| 2016/0041617 A1 | 2/2016 | Poupyrev |
| 2016/0041618 A1 | 2/2016 | Poupyrev |
| 2016/0061942 A1 | 3/2016 | Rao et al. |
| 2016/0061947 A1 | 3/2016 | Patole et al. |
| 2016/0098089 A1 | 4/2016 | Poupyrev |
| 2016/0103213 A1 | 4/2016 | Ikram et al. |
| 2016/0109566 A1 | 4/2016 | Liu et al. |
| 2016/0118353 A1 | 4/2016 | Ahrens et al. |
| 2016/0135655 A1 | 5/2016 | Ahn et al. |
| 2016/0146931 A1 | 5/2016 | Rao et al. |
| 2016/0146933 A1 | 5/2016 | Rao et al. |
| 2016/0178730 A1 | 6/2016 | Trotta et al. |
| 2016/0187462 A1 | 6/2016 | Altus et al. |
| 2016/0191232 A1 | 6/2016 | Subburaj et al. |
| 2016/0223651 A1 | 8/2016 | Kamo et al. |
| 2016/0240907 A1 | 8/2016 | Haroun |
| 2016/0249133 A1 | 8/2016 | Sorensen |
| 2016/0252607 A1 | 9/2016 | Saboo et al. |
| 2016/0259037 A1 | 9/2016 | Molchanov et al. |
| 2016/0266233 A1 | 9/2016 | Mansour |
| 2016/0269815 A1 | 9/2016 | Liao et al. |
| 2016/0291130 A1 | 10/2016 | Ginsburg et al. |
| 2016/0299215 A1 | 10/2016 | Dandu et al. |
| 2016/0306034 A1 | 10/2016 | Trotta et al. |
| 2016/0320852 A1 | 11/2016 | Poupyrev |
| 2016/0320853 A1 | 11/2016 | Lien et al. |
| 2016/0327633 A1 | 11/2016 | Kumar Y.B. et al. |
| 2016/0334502 A1 | 11/2016 | Ali et al. |
| 2016/0349845 A1 | 12/2016 | Poupyrev et al. |
| 2017/0033062 A1 | 2/2017 | Liu et al. |
| 2017/0045607 A1 | 2/2017 | Bharadwaj et al. |
| 2017/0052618 A1 | 2/2017 | Lee et al. |
| 2017/0054449 A1 | 2/2017 | Mani et al. |
| 2017/0055912 A1* | 3/2017 | Gamble ............... A61B 5/0006 |
| 2017/0060254 A1 | 3/2017 | Molchanov et al. |
| 2017/0070952 A1 | 3/2017 | Balakrishnan et al. |
| 2017/0074974 A1 | 3/2017 | Rao et al. |
| 2017/0074980 A1 | 3/2017 | Adib et al. |
| 2017/0090014 A1 | 3/2017 | Subburaj et al. |
| 2017/0090015 A1 | 3/2017 | Breen et al. |
| 2017/0115377 A1 | 4/2017 | Giannini et al. |
| 2017/0131395 A1 | 5/2017 | Reynolds et al. |
| 2017/0139036 A1 | 5/2017 | Nayyar et al. |
| 2017/0141453 A1 | 5/2017 | Waelde et al. |
| 2017/0170947 A1 | 6/2017 | Yang |
| 2017/0176574 A1 | 6/2017 | Eswaran et al. |
| 2017/0192847 A1 | 7/2017 | Rao et al. |
| 2017/0201019 A1 | 7/2017 | Trotta |
| 2017/0212597 A1 | 7/2017 | Mishra |
| 2017/0215734 A1 | 8/2017 | Yamaji |
| 2017/0364160 A1 | 12/2017 | Malysa et al. |
| 2018/0046255 A1 | 2/2018 | Rothera et al. |
| 2018/0055451 A1 | 3/2018 | Kuroyanagi et al. |
| 2018/0071473 A1 | 3/2018 | Trotta et al. |
| 2018/0101239 A1 | 4/2018 | Yin et al. |
| 2018/0279884 A1 | 10/2018 | Ahmad et al. |
| 2019/0302252 A1 | 10/2019 | Santra et al. |
| 2020/0113445 A1 | 4/2020 | Gigie et al. |
| 2020/0367764 A1* | 11/2020 | Le Guillou ........... A61B 5/7278 |
| 2021/0255280 A1 | 8/2021 | Santra et al. |
| 2021/0325509 A1 | 10/2021 | Santra et al. |

FOREIGN PATENT DOCUMENTS

| | | |
|---|---|---|
| CN | 101490578 A | 7/2009 |
| CN | 101585361 A | 11/2009 |
| CN | 102788969 A | 11/2012 |
| CN | 102967854 A | 3/2013 |
| CN | 103529444 A | 1/2014 |

(56) References Cited

FOREIGN PATENT DOCUMENTS

| CN | 203950036 U | 11/2014 |
|---|---|---|
| CN | 106644030 A | 5/2017 |
| CN | 110065499 A | 7/2019 |
| DE | 102008054570 A1 | 6/2010 |
| DE | 102011100907 A1 | 1/2012 |
| DE | 102011075725 A1 | 11/2012 |
| DE | 102014118063 A1 | 7/2015 |
| GB | 2247799 A | 3/1992 |
| JP | 2001174539 A | 6/2001 |
| JP | 2004198312 A | 7/2004 |
| JP | 2006234513 A | 9/2006 |
| JP | 2008029025 A | 2/2008 |
| JP | 2008089614 A | 4/2008 |
| JP | 2009069124 A | 4/2009 |
| JP | 2011529181 A | 12/2011 |
| JP | 2012112861 A | 6/2012 |
| JP | 2013521508 A | 6/2013 |
| JP | 2014055957 A | 3/2014 |
| KR | 20090063166 A | 6/2009 |
| KR | 20140082815 A | 7/2014 |
| WO | 2007060069 A1 | 5/2007 |
| WO | 2013009473 A2 | 1/2013 |
| WO | 2016033361 A1 | 3/2016 |

OTHER PUBLICATIONS

"BT24MTR11 Using BGT24MTR11 in Low Power Applications 24 GHz Rader," Application Note AN341, Revision: Rev 1.0, Infineon Technologies AG, Munich, Germany, Dec. 2, 2013, 25 pages.

Chen, Xiaolong et al., "Detection and Extraction of Marine Target with Micromotion via Short-Time Fractional Fourier Transform in Sparse Domain," IEEE International Conference on Signal Processing, Communications and Computing, ICSPCC, Aug. 5-8, 2016, 5 pages.

Chen, Xiaolong et al., "Detection and Extraction of Target with Micromotion in Spiky Sea Clutter via Short-Time Fractional Fourier Transform", IEEE Transactions on Geoscience and Remote Sensing, vol. 52, No. 2, Feb. 2014, pp. 1002-1018.

Chioukh, Lydia et al., "Noise and Sensitivity of Harmonic Radar Architecture for Remote Sensing and Detection of Vital Signs", IEEE Transactions on Microwave Theory and Techniques, vol. 62, No. 9, Sep. 2014, pp. 1847-1855.

Chuanhua, Du, "FMCW Radar Range-Doppler Processing and Beam Formation Technology," Chinese Doctoral Dissertations & Master's Theses Full Text Database (Masters)—Information Science and Technology Series, China National Knowledge Infrastructure, ISSN 1674-0246, CN 11-9144/G, Dec. 16, 2004-Mar. 2015, 14 pages.

Deacon, Peter et al., "Frequency Modulated Continuous Wave (FMCW) Radar," Design Team 6 Technical Lecture, Nov. 9, 2011, 27 pages.

Dham, Vivek "Programming Chirp Parameters in TI Radar Devices," Application Report SWRA553, Texas Instruments, May 2017, 15 pages.

Diederichs, Kailtyn et al., "Wireless Biometric Individual Identification Utilizing Millimeter Waves", IEEE Sensors Letters, vol. 1, No. 1, IEEE Sensors Council 3500104, Feb. 2017, 4 pages.

Dooring Alert Systems, "Riders Matter," http:Wdooringalertsystems.com, printed Oct. 4, 2017, 16 pages.

Filippelli, Mario et al., "Respiratory dynamics during laughter," J Appl Physiol, (90), 1441-1446, Apr. 2001, http://iap.physiology.org/content/jap/90/4/1441.full.pdf.

Fox, Ben, "The Simple Technique That Could Save Cyclists' Lives," https://www.outsideonline.com/2115116/simple-technique-could-save-cyclists-lives, Sep. 19, 2016, 6 pages.

Gigie, Andrew et al., "Novel Approach for Vibration Detection Using Indented Radar", Progess in Electromagnetic Research C, vol. 87, pp. 147-162, Oct. 4, 2018.

Gouveia, Carolina et al., "A Review on Methods for Random Motion Detection and Compensation in Bio-Radar Systems", Sensors, MDPI, Jan. 31, 2019, 17 pages.

Gu, Changzhan et al., "Assessment of Human Respiration Patterns via Noncontact Sensing Using Doppler Multi-Radar System", Sensors Mar. 2015, 15(3), 6383-6398, doi: 10.3390/s150306383, 17 pages.

Gu, Changzhan et al., "Deep Neural Network based Body Movement Cancellation for Doppler Radar Vital Sign Detection", IEEE MTT-S International Wireless Symposium (IWS) May 19-22, 2019, 3 pages.

Gu, Changzhu "Short-Range Noncontact Sensors for Healthcare and Other Emerginng Applications: A Review", Sensors, MDPI, Jul. 26, 2016, 24 pages.

Gu, Changzhan et al., "From Tumor Targeting to Speed Monitoring", IEEE Microwave Magazine, ResearchGate, Jun. 2014, 11 pages.

Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.

Hu, Wei et al., "Noncontact Accurate Measurement of Cardiopulmonary Activity Using a Compact Quadrature Doppler Radar Sensor", IEEE Transactions on Biomedical Engineering, vol. 61, No. 3, Mar. 2014, pp. 725-735.

Immoreev, I. Ya. "Ultrawideband Radars: Features and Capabilities", Journal of Communications Technology and Electronics, ISSN: 1064-2269, vol. 54, No. 1, Feb. 8, 2009, pp. 1-26.

Inac, Ozgur et al., "A Phased Array RFIC with Built-In Self-Test Capabilities," IEEE Transactions on Microwave Theory and Techniques, vol. 60, No. 1, Jan. 2012, 10 pages.

Killedar, Abdulraheem "XWR1xxx Power Management Optimizations—Low Cost LC Filter Solution," Application Report SWRA577, Texas Instruments, Oct. 2017, 19 pages.

Kishore, N. et al., "Millimeter Wave Antenna for Intelligent Transportation Systems Application", Journal of Microwaves, Optoelectronics and Electromagnetic Applications, vol. 17, No. 1, Mar. 2018, pp. 171-178.

Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 118 pages.

Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.

Li, Changzhi et al., "A Review on Recent Advances in Doppler Radar Sensors for Noncontact Healthcare Monitoring", IEEE Transactions on Microwave Theory and Techniques, vol. 61, No. 5, May 2013, pp. 2046-2060.

Li, Changzhi et al., "A Review on Recent Progress of Portable Short-Range Noncontact Microwave Radar Systems", IEEE Transactions on Microwave Theory and Techniques, vol. 65, No. 5, May 2017, pp. 1692-1706.

Li, Changzhi et al., "Random Body Movement Cancellation in Doppler Radar Vital Sign Detection", IEEE Transactions on Microwave Theory and Techniques, vol. 56, No. 12, Dec. 2008, pp. 3143-3152.

Li, Changzhi et al., "Robust Overnight Monitoring of Human Vital Signs by a Non-contact Respiration and Heartbeat Detector", IEEE Proceedings of the 28th EMBS Annual International Conference, FrA05.5, Aug. 30-Sep. 3, 2006, 4 pages.

Li, Changzhi "Vital-sign monitoring on the go", Sensors news and views, www.nature.com/naturelectronics, Nature Electronics, vol. 2, Jun. 2019, 2 pages.

Lim, Soo-Chul et al., "Expansion of Smartwatch Touch Interface from Touchscreen to Around Device Interface Using Infrared Line Image Sensors," Sensors 2015, ISSN 1424-8220, vol. 15, 16642-16653, doi:10.3390/s150716642, www.mdpi.com/journal/sensors, Jul. 15, 2009, 12 pages.

Lin, Jau-Jr et al., "Design of an FMCW radar baseband signal processing system for automotive application," SpringerPlus a

(56) References Cited

OTHER PUBLICATIONS

SpringerOpen Journal, (2016) 5:42, http://creativecommons.org/licenses/by/4.0/, DOI 10.1186/s40064-015-1583-5; Jan. 2016, 16 pages.

Massagram, Wansuree et al., "Assessment of Heart Rate Variability and Respiratory Sinus Arrhythmia via Doppler Radar", IEEE Transactions on Microwave Theory and Techniques, vol. 57, No. 10, Oct. 2009, pp. 2542-2549.

Mercuri, Marco et al., "Vital-sign monitoring and spatial tracking of multiple people using a contactless radar-based sensor", Nature Electronics, vol. 2, Articles, https://doi.org/10.1038/s41928-019-0258-6, Jun. 2019, 13 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.

Mostov, K., et al., "Medical applications of shortwave FM radar: Remote monitoring of cardiac and respiratory motion", Am. Assoc. Phys. Med., 37(3), Mar. 2010, pp. 1332-1338.

Oguntala, G et al., "Indoor location identification technologies for real-time IoT-based applications: an inclusive survey", Elsevier Inc., http://hdl.handle.net/10454/16634, Oct. 2018, 42 pages.

Peng, Zhengyu et al., "A Portable FMCW Interferometry Radar with Programmable Low-IF Architecture for Localization, ISAR Imaging, and Vial Sign Tracking", IEEE Transactions on Microwave Theory and Techniques, Dec. 15, 2016, 11 pages.

Qadir, Shahida G., et al., "Focused ISAR Imaging of Rotating Target in Far-Field Compact Range Anechoic Chamber," 14th International Conference on Aerospace Sciences & Aviation Technology, ASAT-14-241-IP, May 24-26, 2011, 7 pages.

Richards, Mark A., "Fundamentals of Radar Signal Processing," McGraw Hill Electronic Engineering, ISBN: 0-07-144474-2, Jun. 2005, 93 pages.

Sakamoto, Takuya et al., "Feature-Based Correlation and Topological Similarity for Interbeat Interval Estimation Using Ultrawideband Radar", IEEE Transactions on Biomedical Engineering, vol. 63, No. 4, Apr. 2016, pp. 747-757.

Santra, Avik et al., "Short-range multi-mode continuous-wave radar for vital sign measurement and imaging", ResearchGate, Conference Paper, Apr. 2018, 6 pages.

Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, pp. 815-823.

Simon, W., et al., "Highly Integrated KA-Band Tx Frontend Module Including 8x8 Antenna Array," IMST GmbH, Germany, Asia Pacific Microwave Conference, Dec. 7-10, 2009, 63 pages.

Singh, Aditya et al., "Data-Based Quadrature Imbalance Compensation for a CW Doppler Radar System", ResearchGate, https://www.researchgate.net/publication/258793573, IEEE Transactions on Microwave Theory and Techniques, Apr. 2013, 7 pages.

Suleymanov, Suleyman, "Design and Implementation of an FMCW Radar Signal Processing Module for Automotive Applications," Master Thesis, University of Twente, Aug. 31, 2016, 61 pages.

Thayaparan, T. et al., "Micro-Doppler Radar Signatures for Intelligent Target Recognition," Defence Research and Development Canada, Technical Memorandum, DRDC Ottawa TM 2004-170, Sep. 2004, 73 pages.

Thayaparan, T. et al., "Intelligent target recognition using micro-Doppler radar signatures," Defence R&D Canada, Radar Sensor Technology III, Proc. of SPIE, vol. 7308, 730817, Dec. 9, 2009, 11 pages.

Tu, Jianxuan et al., "Fast Acquisition of Heart Rate in Noncontact Vital Sign Radar Measurement Using Time-Window-Variation Technique", IEEE Transactions on Instrumentation and Measurement, vol. 65, No. 1, Jan. 2016, pp. 112-122.

Zakrzewski, M. et al., "Quadrature Imbalance Compensation with Ellipse-Fitting Methods for Microwave Radar Physiological Sensing," IEEE Transactions on Microwave Theory and Techniques, vol. 62, No. 6, Jun. 2014, 10 pages.

Vinci, Gabor et al., "Microwave Interferometer Radar-Based Vital Sign Detection for Driver Monitoring Systems", IEEE MTT-S International Conference on Microwaves for Intelligent Mobility, Apr. 27-29, 2015, 4 pages.

Vinci, Gabor et al., "Six-Port Radar Sensor for Remote Respiration Rate and Heartbeat Vital-Sign Monitoring", IEEE Transactions on Microwave Theory and Techniques, vol. 61, No. 5, May 2013, pp. 2093-2100.

Wang, Fu-Kang et al., "Wrist Pulse Rate Monitor Using Self-Injection-Locked Radar Technology", Biosensors, MDPI, Oct. 26, 2016, 12 pages.

Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, pp. 18-34.

Will, Christoph et al., "Advanced Template Matching Algorithm for Instantaneous Heartbeat Detection using Continuous Wave Radar Systems", ResearchGate, May 2017, 5 pages.

Will, Christoph et al., "Human Target Detection, Tracking, and Classification Using 24-GHz FMCW Radar", IEEE Sensors Journal, vol. 19, No. 17, Sep. 1, 2019, pp. 7283-7299.

Will, Christoph et al., "Local Pulse Wave Detection using Continuous Wave Radar Systems", IEEE Journal of Electromagnetics, RF and Microwaves in Medicine and Biology, Oct. 25, 2017, 9 pages.

Will, Christoph et al., "Radar-Based Heart Sound Detection", Scientific Reports, www.nature.com/scientificreports, Jul. 26, 2018, 15 pages.

Xin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, Apr. 15, 2014, 11 pages.

* cited by examiner

US 11,614,516 B2

RADAR VITAL SIGNAL TRACKING USING A KALMAN FILTER

TECHNICAL FIELD

The present disclosure relates generally to an electronic system and method, and, in particular embodiments, to a radar vital signal tracking using a Kalman filter.

BACKGROUND

Applications in the millimeter-wave frequency regime have gained significant interest in the past few years due to the rapid advancement in low cost semiconductor technologies, such as silicon germanium (SiGe) and fine geometry complementary metal-oxide semiconductor (CMOS) processes. Availability of high-speed bipolar and metal-oxide semiconductor (MOS) transistors has led to a growing demand for integrated circuits for millimeter-wave applications at e.g., 24 GHz, 60 GHz, 77 GHz, and 80 GHz and also beyond 100 GHz. Such applications include, for example, automotive radar systems and multi-gigabit communication systems.

In some radar systems, the distance between the radar and a target is determined by transmitting a frequency modulated signal, receiving a reflection of the frequency modulated signal (also referred to as the echo), and determining a distance based on a time delay and/or frequency difference between the transmission and reception of the frequency modulated signal. Accordingly, some radar systems include a transmit antenna to transmit the radio-frequency (RF) signal, and a receive antenna to receive the reflected RF signal, as well as the associated RF circuits used to generate the transmitted signal and to receive the RF signal. In some cases, multiple antennas may be used to implement directional beams using phased array techniques. A multiple-input and multiple-output (MIMO) configuration with multiple chipsets can be used to perform coherent and non-coherent signal processing as well.

SUMMARY

In accordance with an embodiment, a method includes: receiving reflected radar signals with a millimeter-wave radar; generating a displacement signal indicative of a displacement of a target based on the reflected radar signals; filtering the displacement signal using a bandpass filter to generate a filtered displacement signal; determining a first rate indicative of a heartbeat rate of the target based on the filtered displacement signal; tracking a second rate indicative of the heartbeat rate of the target with a track using a Kalman filter; updating the track based on the first rate; and updating a setting of the bandpass filter based on the updated track.

In accordance with an embodiment, a device includes: a millimeter-wave radar configured to transmit chirps and receive reflected chirps; and a processor configured to: generate a displacement signal indicative of a displacement of a target based on the reflected chirps, filter the displacement signal using a bandpass filter to generate a filtered displacement signal, determine a first rate indicative of a heartbeat rate of the target based on the filtered displacement signal, track a second rate indicative of the heartbeat rate of the target with a track using a Kalman filter, update the track based on the first rate, and update a setting of the bandpass filter based on the updated track.

In accordance with an embodiment, a method for tracking a vital rate indicative of a heartbeat rate of a human target using a track of a Kalman filter, the method including: receiving reflected radar signals; generating a displacement signal indicative of a displacement of a target based on the reflected radar signals; filtering the displacement signal using a bandpass filter to generate a filtered displacement signal; generating a heartbeat rate estimate based on the filtered displacement signal; determining a heartbeat rate prediction and an uncertainty prediction based on the track; determining whether the heartbeat rate estimate is an outlier based on the uncertainty prediction; and when the heartbeat rate estimate is determined to be not an outlier, updating the track based on the heartbeat rate estimate; and updating a setting of the bandpass filter based on the updated track.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in different figures generally refer to corresponding parts unless otherwise indicated. The figures are drawn to clearly illustrate the relevant aspects of the preferred embodiments and are not necessarily drawn to scale.

DETAILED DESCRIPTION OF ILLUSTRATIVE EMBODIMENTS

Figure 1:
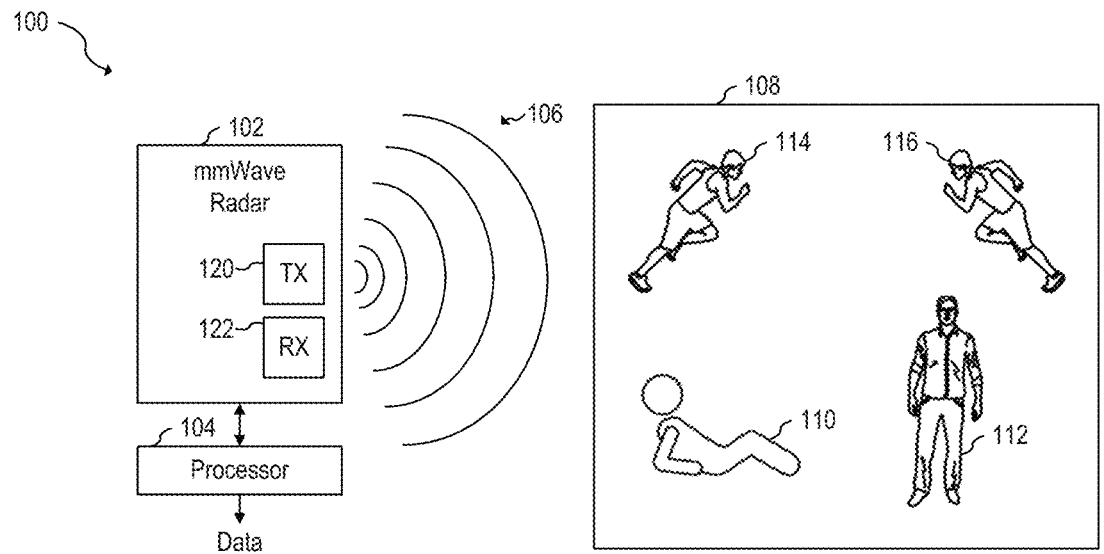
FIG. 1 shows a radar system, according to an embodiment of the present invention.

The making and using of the embodiments disclosed are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The description below illustrates the various specific details to provide an in-depth understanding of several example embodiments according to the description. The embodiments may be obtained without one or more of the specific details, or with other methods, components, materials and the like. In other cases, known structures, materials or operations are not shown or described in detail so as not to obscure the different aspects of the embodiments. References to "an embodiment" in this description indicate that a particular configuration, structure or feature described in relation to the embodiment is included in at least one embodiment. Consequently, phrases such as "in one embodiment" that may appear at different points of the present description do not necessarily refer exactly to the same embodiment. Furthermore, specific formations, structures or features may be combined in any appropriate manner in one or more embodiments.

Embodiments of the present invention will be described in a specific context, a system and method for heartbeat tracking of a human using a Kalman Filter. Embodiments of the present invention may be used for other vital signs tracking, such as respiration, as well as for other targets, such as a dog, or other animals.

Embodiments of the present invention may be used in a variety of applications. For example, some embodiments may be used in patient monitoring in hospitals, sleep apnea detection, presence sensing in homes and offices, driver monitoring in autonomous cars, and physiological monitoring in surveillance and earthquake rescue operations. Other applications are also possible.

In an embodiment of the present invention, a millimeter-wave radar system enables a contactless, non-invasive method to monitor and track the heartbeat of a human target using a Kalman filter that applies a band-pass filter to a time-domain heartbeat signal to generate a filtered signal from which the heartbeat rate is estimated. After a coarse estimation of the heartbeat rate, a bandwidth of the applied band-pass filter is successively updated (e.g., narrowed) based on respective successive estimations of the heartbeat rate. In some embodiments, measurement segments with random body movements are identified and ignored for the Kalman filter update.

Advantages of some embodiments include high accuracy heartbeat rate determination during only a short observation window. Some embodiments advantageously prevent jumps in the determined heartbeat rate.

Monitoring the vital signs of, e.g., human targets finds wide usage in the fields of, e.g., consumer electronics, medical care, surveillance, driver assistance, and industrial applications.

A radar, such as a millimeter-wave radar, may be used to detect and track humans. Once the human targets are identified, the radar may be used to monitor vital signs such as the heartbeat rate of the identified human targets. In some embodiments, therefore, a radar, such as a millimeter-wave radar, enables a contactless, non-invasive method for vital sensing, which may advantageously increase the comfort of the human target during the vital signs monitoring.

FIG. 1 shows radar system 100, according to an embodiment of the present invention. Radar system 100 includes millimeter-wave radar 102 and processor 104. In some embodiments, millimeter-wave radar 102 includes processor 104.

During normal operation, millimeter-wave radar 102 transmits a plurality of radiation pulses 106, such as chirps, towards scene 108 with transmitter (TX) circuit 120. In some embodiments the chirps are linear chirps (i.e., the instantaneous frequency of the chirp varies linearly with time).

The transmitted radiation pulses 106 are reflected by objects in scene 108. The reflected radiation pulses (not shown in FIG. 1), which are also referred to as the echo signal, are received by millimeter-wave radar 102 using receiver (RX) circuit 122 and processed by processor 104 to, for example, detect and track targets such as humans.

The objects in scene 108 may include static humans, such as lying human 110, humans exhibiting low and infrequent motions, such as standing human 112, and moving humans, such as running or walking humans 114 and 116. The objects in scene 108 may also include static objects (not shown), such as furniture, and periodic movement equipment. Other objects may also be present in scene 108.

Processor 104 analyses the echo data to determine the location of humans using signal processing techniques. For example, in some embodiments, a range FFT is used for estimating the range component of the location of a detected human (e.g., with respect to the location of the millimeter-wave radar). The azimuth component of the location of the detected human may be determined using angle estimation techniques.

In some embodiments, a range-Doppler map (image) is generated from the echo data, and a two-dimensional (2D) moving target identification (MTI) is performed on the range-Doppler map to detect moving targets.

Processor 104 may be implemented as a general purpose processor, controller or digital signal processor (DSP) that includes, for example, combinatorial circuits coupled to a memory. In some embodiments, the DSP may be implemented with an ARM architecture, for example. In some embodiments, processor 104 may be implemented as a custom application specific integrated circuit (ASIC). Some embodiments may be implemented as a combination of hardware accelerator and software running on a DSP or general purpose micro-controller. Other implementations are also possible.

Millimeter-wave radar 102 operates as a frequency-modulated continuous-wave (FMCW) radar that includes a millimeter-wave radar sensor circuit, and one or more antenna(s). Millimeter-wave radar 102 transmits (using TX 120) and receives (using RX 122) signals in the 20 GHz to 122 GHz range via the one or more antenna(s) (not shown). Some embodiments may use frequencies outside of this range, such as frequencies between 1 GHz and 20 GHz, or frequencies between 122 GHz, and 300 GHz.

In some embodiments, the echo signals received by millimeter-wave radar 102 are filtered and amplified using band-pass filter (BPFs), low-pass filter (LPFs), mixers, low-noise amplifier (LNAs), and intermediate frequency (IF) amplifiers in ways known in the art. The echo signals are then digitized using one or more analog-to-digital converters (ADCs) for further processing. Other implementations are also possible.

Generally, monitoring a heartbeat signal of a human target with a radar-based system is a complex endeavor. For example, the amplitude of the heartbeat signal is generally smaller than the amplitude of the respiration signal of the human target. The amplitude of the heartbeat signal is also smaller than the amplitude caused by the movement of the human target (e.g., when walking), as well as random body movements of the human target (e.g., such lifting an arm, twisting the torso, etc.). Additionally, the signal shape of a single heartbeat may be dependent on the subject, the chosen measurement spot, and the distance to the antenna.

In an embodiment of the present invention, a pre-processing step is performed in which data inflicted by random body movements are identified. During an adaptive heartbeat rate filtering and monitoring step, a band-pass filter is applied to a time-domain heartbeat signal to generate a filtered signal, from which the heartbeat rate is determined. The determined heartbeat rate per time instance is stabilized and smoothed by applying a Kalman filter, which additionally updates the bandpass filter limits. In some embodiments, when data inflicted by random body movement is detected, the Kalman filter is not updated with the new measurements and, instead, the state prediction of the Kalman filter is applied.

In some embodiments, identifying data inflicted by random body movements advantageously allows for preventing jumps in the determined heartbeat rate. In some embodiments, performing a time-domain (band-pass) filtering of the time-domain heartbeat signal advantageously allows for fast and accurate identification of the heartbeat signal from other signals, such as the respiration signal.

Figure 2:
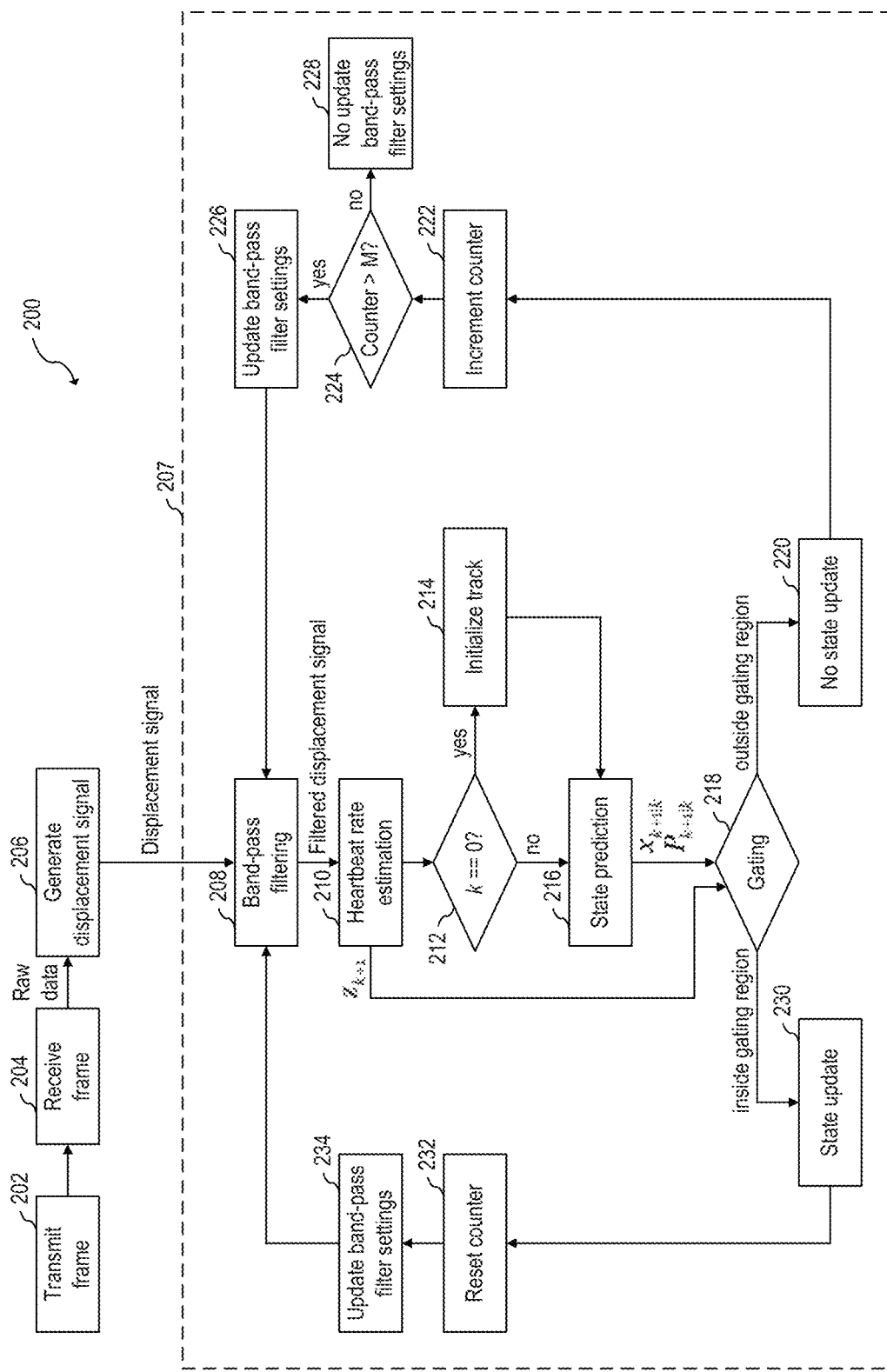
FIG. 2 shows a flow chart of an embodiment method for determining a heartbeat rate of a human target, according to an embodiment of the present invention.

FIG. 2 shows a flow chart of embodiment method 200 for determining a heartbeat rate of a human target, according to an embodiment of the present invention. Method 200 may be implemented, for example, by FMCW radar system 100.

During step 202, millimeter-wave radar 102 transmits a frame of chirps (106) towards scene 108. The time between chirps of a frame is generally referred to as pulse repetition time (PRT). In some embodiments, the time interval between the end of the last chirp of a frame and the start of the first chirp of the next frame is the same as the PRT so that all chirps are transmitted (and received) equidistantly.

In some embodiments, the chirps have a bandwidth of 2 GHz within the 60 GHz UWB band, the frame time has a duration of 1.28 s, and the PRT is 5 ms (corresponding to an effective sampling rate of 200 Hz).

During step 204, raw data is generated based on the reflected chirps received by millimeter-wave radar 102. For example, in some embodiments, during step 204, the received radar signal is mixed with the transmitted radar signals to generate an IF signal that is low-pass filtered and digitized with an ADC to generate the raw data.

During step 206, a displacement signal of a human target is generated, where the displacement signal is a time-domain signal. The displacement signal is indicative of a vital sign, such as heartbeat or respiration, for example. For example, small movements in the chest of a human target may be indicative of a vital sign of the human target. In some embodiments, and as explained later, e.g., with respect to FIG. 3, the displacement signal of a human target is generated by calculating arctangent function of the baseband signal from the millimeter-wave radar, as arctan(Q/I), e.g., as given by Equation 15.

During step 207, the displacement signal generated during step 206 is processed to determine, e.g., the heartbeat of a human target. As shown in FIG. 2, step 207 includes steps 208, 210, 212, 214, 216, 218, 220, 222, 224, 226, 228, 230, 232, and 234.

As will be explained in greater detail below, during step 207, a first rate indicative of the heartbeat of the human target is determined (e.g., measured) from the displacement signal (in step 210). A second rate indicative of the heartbeat of the human target is predicted by predicting the heartbeat rate based on a track of a Kalman filter (i.e., based on the history of previous heartbeat rate determinations for the human target by the Kalman filter) but without considering the current first rate (in step 216). If it is determined based on the predicted second rate that the first rate is acceptable (in step 218), the track of the Kalman filter is updated (in step 230) to include information from the first rate and the bandpass filter is updated (in step 234) based on the updated track. If it is determined based on the predicted second rate that the first rate is not acceptable (in step 218), the track of the Kalman filter is not updated (in step 220) to include information from the first rate.

During step 208, the displacement signal is filtered with a band-pass filter. In some embodiments, a fourth order Butterworth digital filter is applied to the displacement signal. A filter of different order and/or different type may also be applied.

In some embodiments, the default pass-band of the band-pass filter is from 0.7 Hz to 3 Hz. In some embodiments, the passband of the band-pass filter is may be dynamically change within the initial default range (e.g., between 0.7 Hz and 3 Hz). In some embodiments, the pass-band may be outside this frequency range, such as having a lower cutoff frequency $f_L$ of 0.65 Hz or lower and/or higher cutoff frequency $f_H$ higher than 3 Hz, such as 3.5 Hz, or higher.

During step 210, the first rate $z_{k+1}$ indicative of the heartbeat rate of the human target is determined, e.g., estimated, based on the filtered displacement signal, where k+1 is indicative of the next time step of the Kalman filter, which is currently being evaluated. For example, in some embodiments, the first rate $z_{k+1}$ is estimated by counting the number of peaks in the filtered displacement signal. In some embodiments, the first rate $z_{k+1}$ may be estimated based on the time between peaks of the filtered displacement signal. In some embodiments, the first rate $z_{k+1}$ may also be estimated through template matching and estimating the frequency peaks. Other implementations are also possible.

When the first rate $z_{k+1}$ is recorded during the first time step k=0 (in step 212), a track of a Kalman filter is initialized during step 214. In some embodiments, k may correspond to a single frame or to a group of frames (such as 8 frames, for example). As will be explained in greater detail later, the Kalman filter keeps track of the state of the heartbeat rate of the target for every $k^{th}$ update.

Kalman filtering may be understood as a recursive Bayesian process, which may be applied when the measured values contain unpredictable or random errors, uncertainties or variations. With respect to FIG. 2, the process of Kalman filtering includes steps 212, 214, 216, and 230. The process of Kalman filtering may also include steps 218 and 220.

The state vector x used by the Kalman filter may be expressed as $$x=[h \ \dot{h} \ \ddot{h}]^T \quad (1)$$

where h, $\dot{h}$, and $\ddot{h}$ represents the second rate indicative of the heartbeat rate of the human target in Hz, its first order derivative, and its second order derivative, respectively.

The state vector in the Kalman filter at time step k may be represented as a Gaussian process with mean $x_{k|k}$ and covariance or uncertainty $P_{k|k}$. The vector $x_{k|k}$ includes the second rate $h_k$.

In some embodiments, the Kalman filter used is designed with a constant acceleration model, in which predicting the state in time step k+1 from state vector in time step k is given by $$x_{k+1|k} = Ax_{k|k} \quad (2)$$

where $$A = \begin{bmatrix} 1 & \Delta t & 0.5\Delta t^2 \\ 0 & 1 & \Delta t \\ 0 & 0 & 1 \end{bmatrix} \quad (3)$$

where $\Delta t$ is the time elapsed between two time steps of the Kalman filter.

The observation model may be given by $$y_{k+1}=Hx_{k+1|k} \quad (4)$$

where $$H=[1 \ 0 \ 0] \quad (5)$$

In some embodiments, the uncertainty Q of the state prediction originates from process noise, which may be modeled as $$Q=GG^T\rho_a^2 \quad (6)$$

where $\rho_a^2$ represents the acceleration process noise, and where $$G=[0.5\Delta t^2\ \Delta t\ 1] \quad (7)$$

The variance of the measurement noise may be given by $R=\delta h^2$, which represents the expected square of the estimation error.

During step 214, the track may be initialized with default Q, R noise matrices and initial state and covariance $x_{o|o}$, $P_{o|o}$, along with default band-pass filter settings.

During step 216, for each time step k, the Kalman filter makes a state prediction based on the track associated with the heartbeat rate of the human target. In some embodiment, the state prediction may be determined by $$x_{k+1|k}=Ax_{k|k}$$

$$P_{k+1|k}=AP_{k|k}A^T+Q \quad (8)$$

where the state prediction includes a prediction of the second rate ($h_{k+1}$) as part of the state prediction $x_{k+1|k}$, e.g., as shown in Equations 1 and 8. The prediction of the second rate ($h_{k+1}$) may also be referred to as the heartbeat rate prediction.

In some embodiments, when k>0, step 216 may be performed, before, after, or concurrently with step 210.

During step 218, an ellipsoidal gating function checks whether the first rate $z_{k+1}$ (also referred to as the heartbeat rate estimate $z_{k+1}$) is within a gating window. The gating function may be given by $$(z_{k+1}-y_{k+1})^T P_{k+1|k}^{-1}(z_{k+1}-y_{k+1})>\gamma$$

$$(z_{k+1}-y_{k+1})^T P_{k+1|k}^{-1}(z_{k+1}-y_{k+1})<\gamma \quad (9)$$

where $y_{k+1}$ is given by Equation 4, and where $\gamma$ is the gate threshold. When the heartbeat rate estimate $z_{k+1}$ is outside the gating region (i.e., when the gating function is higher than $\gamma$), the state of the Kalman filter is not updated (during step 220) based on the heartbeat rate estimate $z_{k+1}$ (since the new heartbeat rate estimate $z_{k+1}$ is an outlier, and, therefore there is no target detected associated to the track).

During step 222, a counter is incremented to keep track of the number of time steps in which the first rate $z_{k+1}$ falls outside the gating region. If it is determined during step 224 that there have been more than M consecutive instances in which the first rate $z_{k+1}$ is outside the gating region (e.g., the counter count is higher than M), then the band-pass filter settings are updated during step 226. For example, in some embodiments, the band-pass filter pass-band is set to a default value, such as from 0.7 Hz to 3 Hz. In other embodiments, the pass-band is incrementally broadened each time step 226 is performed (e.g., by increasing the pass-band by a predetermined amount, such as 0.5 Hz, or a predetermined percentage, such as 10%, until reaching a predetermined maximum, such as the default value).

In some embodiments, the settings of the band-pass filter are updated based on the state prediction (e.g., from Equation 8) during step 226. For example, in some embodiments, during step 226, the lower cutoff frequency $f_L$ and higher cutoff frequency $f_H$ of the band-pass filter are updated as $$f_L=h_{k+1|k}-\sqrt{P_{k+1|k}(1,1)}$$

$$f_H=h_{k+1|k}+\sqrt{P_{k+1|k}(1,1)} \quad (10)$$

In some embodiments, updating the pass-band filter based on Equation 10 advantageously allows for detecting a heartbeat rate that might have drifted during the period that there were no updates. In some embodiments, the track is killed and the filter settings reset to default values when there is not target detections for N consecutive time steps of the Kalman filter. In some embodiments, M is equal to 5 and N is equal to 5. Other values may also be used.

If it is determined during step 224 that the counter count is not higher than M during step 224, then the band-pass filter settings are not updated during step 228.

When the heartbeat rate estimate $z_{k+1}$ is inside the gating region (i.e., when the gating function is lower than $\gamma$), the state of the Kalman filter is updated (during step 230) based on the first rate $z_{k+1}$. For example, in some embodiments, the state of the Kalman filter is updated by $$x_{k+1|k+1}=x_{k+1|k}+K_{k+1}(z_{k+1}-y_{k+1})$$

$$P_{k+1|k+1}=(I-K_kH)P_{k+1|k} \quad (11)$$

where I is the identify matrix and $K_{k+1}$ is given by $$K_{k+1}=P_{k+1|k}H^T(HP_{k+1|k}H^T+R)^{-1} \quad (12)$$

During step 232, the counter is reset. As shown, steps 232, 222, and 224 are used to keep track of consecutive instances in which the first rate $z_{k+1}$ is outside the gating region. Some embodiments may keep track of consecutive instances in which the first rate $z_{k+1}$ is outside the gating region in other ways.

During step 234, the settings of the band-pass filter are updated based on the updated state (e.g., from Equation 11). For example, in some embodiments, during step 234, the lower cutoff frequency $f_L$ and higher cutoff frequency $f_H$ of the band-pass filter are updated as $$f_L=h_{k+1|k+1}-\sqrt{P_{k+1|k+1}(1,1)}$$

$$f_H=h_{k+1|k+1}+\sqrt{P_{k+1|k+1}(1,1)} \quad (13)$$

In some embodiments, the lower cutoff frequency $f_L$ and higher cutoff frequency $f_H$ of the band-pass filter are updated as $$f_L=h_{k+1|k+1}-\alpha\sqrt{P_{k+1|k+1}(1,1)}$$

$$f_H=h_{k+1|k+1}+\alpha\sqrt{P_{k+1|k+1}(1,1)} \quad (14)$$

where $\alpha$ is a real number, such as between, e.g., 0.5 and 3.

In some embodiments, the pass-band of the band-pass filter is updated so that it is centered at the frequency of the current heartbeat rate estimate $z_{k+1}$.

As illustrated in FIG. 2, some embodiments use an adaptive bandpass filtering to extract the heartbeat rate signal along with Kalman filter-based tracking procedure. In some embodiments, the combination of these steps leads to narrowing of the pass-band range of the band-pass filter while simultaneously approximating the actual heartbeat rate as the center frequency of the pass-band.

In some embodiments, performing adaptive bandpass filtering in combination with Kalman filter-based tracking and the use of, e.g., ellipsoidal gating advantageously allows for minimizing the impact of intermodulation product, e.g., caused by the combination of the heartbeat signal, the respiration signal, and harmonics thereof.

Figure 3:
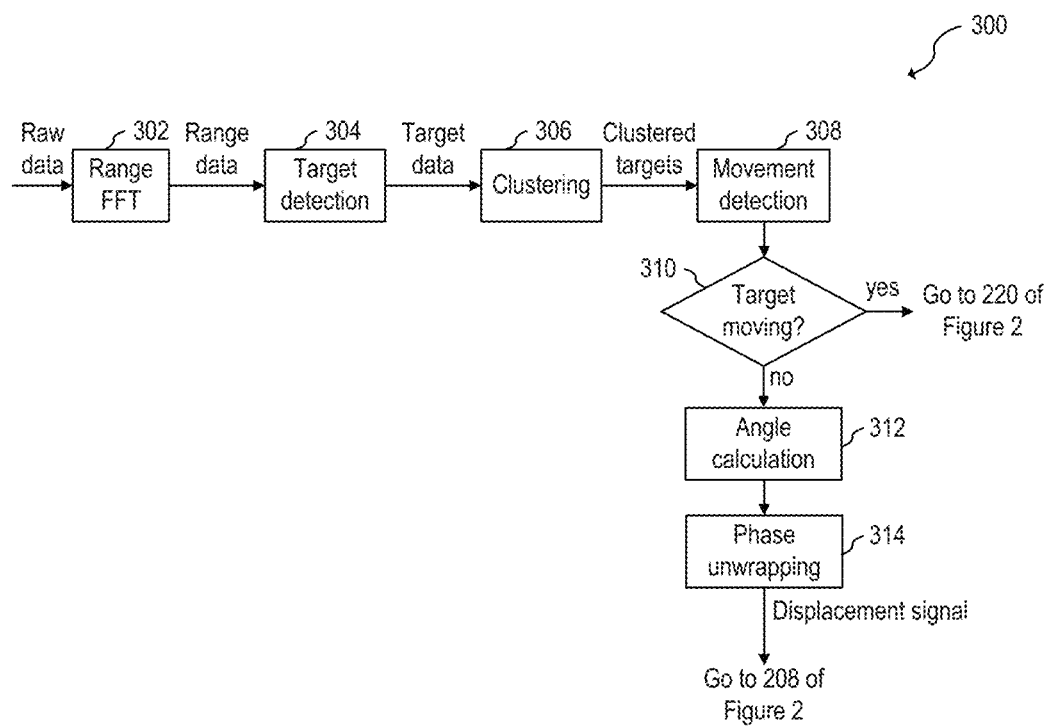
FIG. 3 shows a flow chart of an embodiment method for generating a displacement signal for determining a heartbeat rate of a human target, according to an embodiment of the present invention.

FIG. 3 shows a flow chart of embodiment method 300 for generating a displacement signal for determining a heartbeat rate of a human target, according to an embodiment of the present invention. Step 206 may be implemented as method 300.

During step 302, a range FFT is performed on the raw data, where the maximum unambiguousness range for the range FFT is based on the PRT, the number of samples per chirp, chirp time, and sampling rate of the analog-to-digital converter (ADC). In some embodiments, the ADC has 12 bits. ADC's with different resolution, such as 10 bits, 14 bits, or 16 bits, for example, can also be used.

In some embodiments, the range FFT is applied on all samples of the observation window. The observation window may be implemented as consecutive windows or as sliding windows and may have a length of one or more frames. For example, in some embodiments, the observation window is implemented as a sliding window in which the length of the observation window is a plurality of time steps which are evaluated during each time step. For example, in an embodiment in which the time step is equal to 1 frame, and the observation window is a sliding window with 8 frames, then, for each frame, the last 8 frames are used as the observation window. In an embodiment, an observation window with a duration of 8 frames has a duration of about 10 s.

In some embodiments, the observation window is equal to the duration of the time step k (which may be one or more frames).

In some embodiments, range data, such as a range image, such as a range-Doppler image or a range cross-range image is generated during step 302.

During step 304, detection of potential targets is performed. For example, in some embodiments, an order statistics (OS) constant false alarm rate (CFAR) (OS-CFAR) detector is performed during step 304. The CFAR detector generates target detection data (also referred to as target data) in which, e.g., "ones" represent targets and "zeros" represent non-targets based, e.g., on the power levels of the range image. For example, in some embodiments, the CFAR detector compares the power levels of the range-Doppler image with a threshold, and points above the threshold are labeled as targets while points below the threshold are labeled as non-targets. Although targets may be indicated by ones and non-targets may be indicated by zeros, it is understood that other values may be used to indicate targets and non-targets.

Targets present in the target data are clustered during step 306 to generate clustered targets (since, e.g., a human target may occupy more than one range bin). For example, in an embodiment, a density-based spatial clustering of applications with noise (DBSCAN) algorithm is used to associate targets to clusters during step 306. The output of DBSCAN is a grouping of the detected points into particular targets. DBSCAN is a popular unsupervised algorithm, which uses minimum points and minimum distance criteria to cluster targets, and may be implemented in any way known in the art. Other clustering algorithms may also be used.

During step 308, movement detection of the clustered targets is performed. For example, in some embodiments, the complex FFT output is stored in a sliding window. Then, the amplitude of each range bin is summed up along the complete sliding window. The peak in the complete sliding window within chosen minimum and maximum ranges is the target range bin for the current frame.

In some embodiments, data is not further processed (e.g., with respect to method 200, go from step 206 directly to step 220) if the standard deviation in the target range bin along the sliding window is above a predetermined threshold (movement detection). For example, in some embodiments, if it determined during step 310 that the human target is moving (if the standard deviation in the target range bin along the sliding window is above a predetermined threshold), data from the current frame may not be further processed (e.g., and step 220 of FIG. 2 may be performed next).

If it is determined during step 310 that the human target is not moving (if the standard deviation in the target range bin along the sliding window is below the predetermined threshold), the displacement signal may be determined, e.g., during steps 312 and 314. It is understood that when it is determined during step 310 that the target is not moving, the target may be exhibiting some movement, such as movements of the target's hands outside the field of view of the radar, or any other movement that results in a standard deviation below the predetermined threshold. Such may be the case, for example, of a human target that is sitting or standing, for example.

During step 312, the angle of the compensated target data is calculated by arctangent demodulation of the signal from the selected range bin selected during step 304 (the detected target) and that is determined to be not moving during step 310. The resulting phase values in the range of $[-\pi,+\pi]$ are unwrapped between two consecutive data points during step 314. For example, during step 314, the phase is unwrapped by adding or subtracting $2\pi$ for phase jumps larger than $-\pi$ or $+\pi$, respectively.

With $\lambda$ being the wavelength of the carrier frequency and $\lambda/2$ representing the unambiguousness (phase) range, the displacement of the human target can subsequently be calculated by $$\Delta d = \frac{\lambda}{4\pi} \cdot \text{unwrap}\left(\arctan\frac{Q}{I}\right) \quad (15)$$

where I and Q are the in-phase and quadrature-phase components of the carrier, respectively.

As illustrated in FIG. 3, some embodiments advantageously improve the quality of the heartbeat estimate by avoiding the update of the state of the Kalman filter when the human target is moving.

Some embodiments may track the heartbeat of multiple human targets simultaneously by using multiple tracks of the Kalman filter.

FIGS. 4A-4D illustrate test results of a millimeter-wave radar system implementing method 200, according to an embodiment of the present invention. The test results were performed on a millimeter-wave radar system similar to millimeter-wave radar system 100, and using chirps having a bandwidth of 2 GHz within the 60 GHz UWB band, having a PRT of 5 ms, a frame time of 1.28 s, an observation window of 8 frames (implemented as a sliding window), an ADC having a 12 bit resolution, and seven human targets placed in front of the millimeter-wave radar at a distance of about 40 cm from the radar. A chest belt was used as a reference heartbeat rate sensor. For the test, all measurement rows have a length of 16 frames, corresponding to approximately 20 s.

Figure 4A:
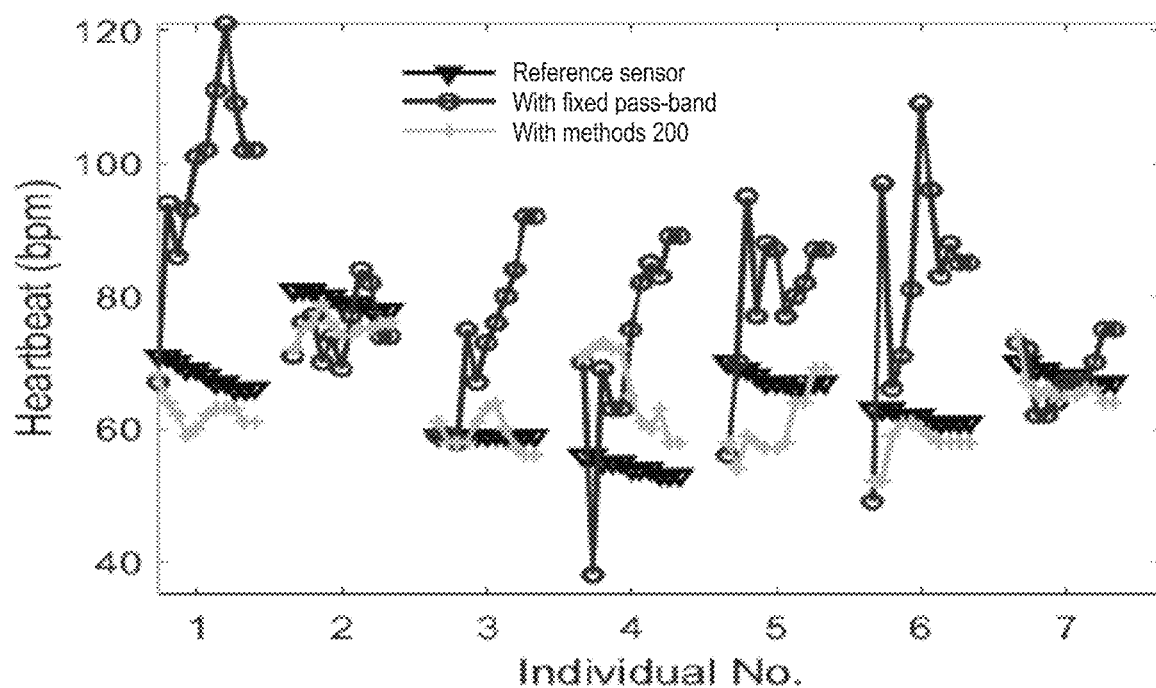
FIGS. 4A-4D illustrate test results of a millimeter-wave radar system implementing the method of FIG. 2, according to an embodiment of the present invention.
Figure 4B:
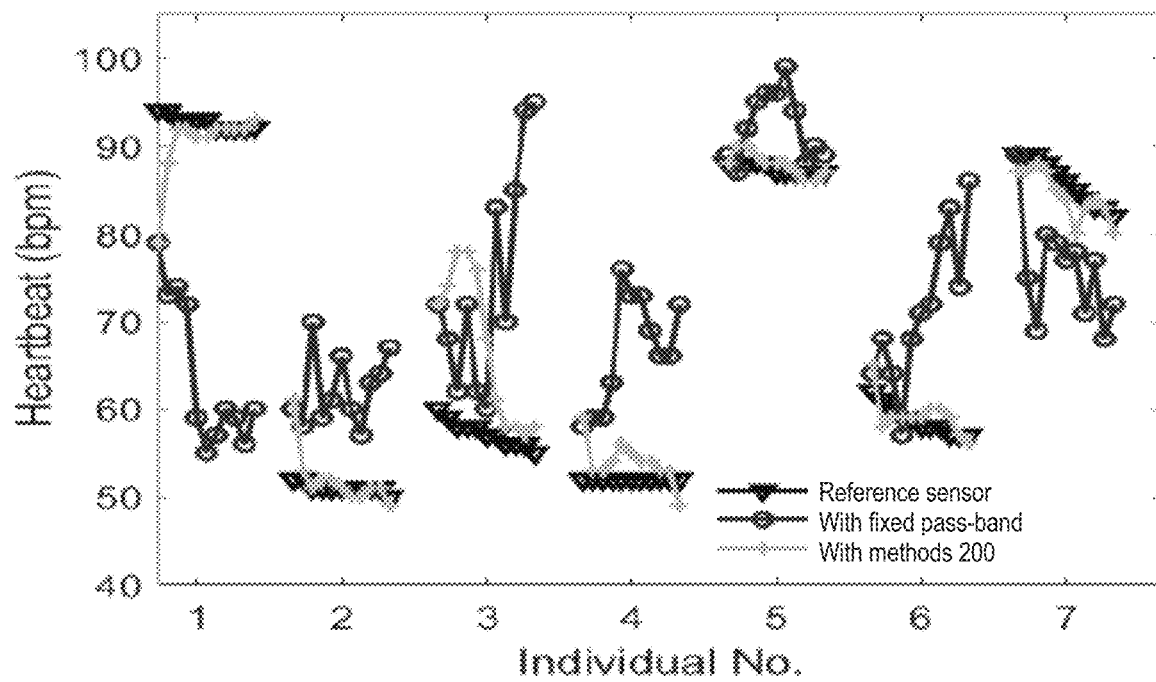

FIGS. 4A and 4B show the heartbeat rate of seven human targets during breath-holding, and with common breathing, respectively.

As shown in FIGS. 4A and 4B, in some embodiments, method 200 achieves better results (for all measurement rows) than methods using a fixed pass-band for the band-pass filter. For example, methods using a fixed pass-band for the band-pass filter show a high deviation from the reference sensor and sometimes have large jumps between consecutive values.

As shown, in some embodiments, narrowing down the bandwidth of the pass-band of the band-pass filter and tracking the heartbeat rate value advantageously prevent such jumps and smooth the estimated values (output of step 210). While the first values may show a considerable deviation from the reference sensor, the Kalman filtering approximates the values towards the reference in each step. The resulting root-mean-square error (RMSE) for the embodiment tested are 5.3 bpm (FIG. 4A) and 7.0 bpm (FIG. 4B) compared to 17.6 bpm (FIG. 4A), and 21.3 bpm (FIG. 4A) for the radar system with fixed pass-band.

Figure 4C:
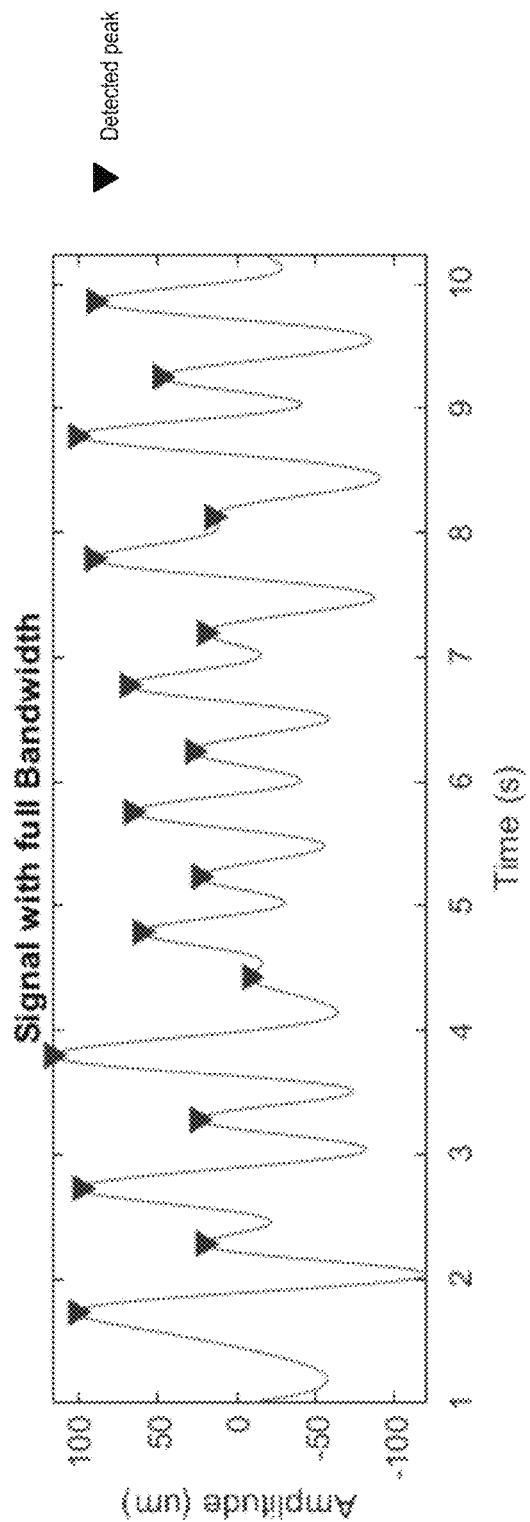
Figure 4D:
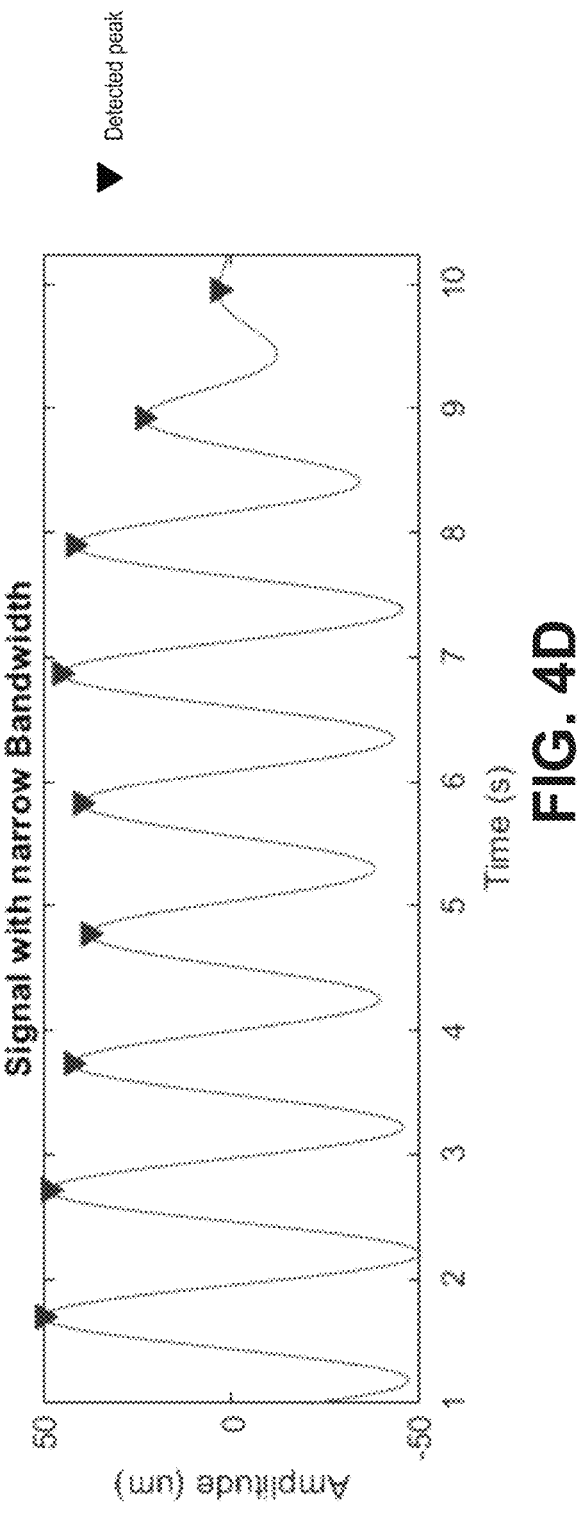

FIGS. 4C and 4D show a filtered displacement signal (output of step 208) with fixed pass-band limits and with adaptive pass-band limits (by applying method 200), respectively. During the time window shown in FIGS. 4C and 4D, the human target has a heartbeat rate of 59 bpm. As shown, the filtered displacement signal of FIG. 4C (which has a pass-band from 0.7 Hz to 3 Hz) results in a heartbeat rate of 117 bpm due to the many peak detections (which may be the result of, harmonics, the respiration rate, and/or intermodulation of between the respiration rate, heartbeat rate, and harmonics thereof, for example). In contrast, the filtered displacement signal that is adaptively filtered using method 200 results in more accurate heartbeat rate measurement of 58 bpm, as shown in FIG. 4D.

Figure 5:
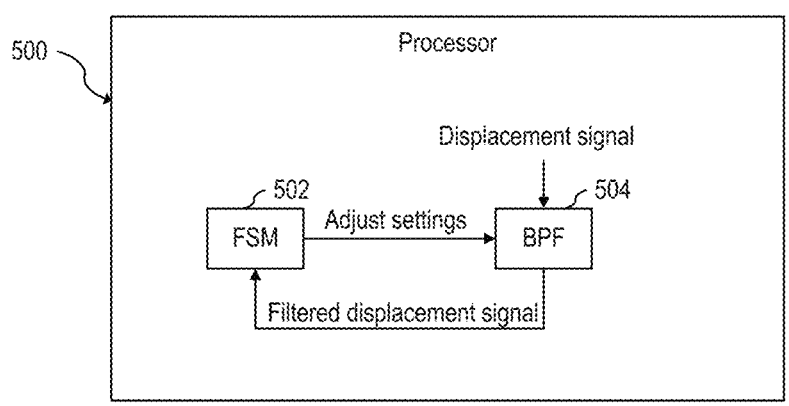
FIG. 5 shows a schematic diagram of the processor of FIG. 1, according to an embodiment of the present invention.

FIG. 5 shows a schematic diagram of processor 500, according to an embodiment of the present invention. Processor 104 may be implemented as processor 500.

As shown, processor 500 includes digital band-pass filter 504, finite state machine (FSM) 502, and memory 506. In some embodiments, band-pass filter 504 is configured to perform step 208, while FSM 702 is configured to perform steps 210, 212, 214, 216, 218, 220, 222, 224, 226, 228, 230, 232, and 234. Other implementations are also possible.

Example embodiments of the present invention are summarized here. Other embodiments can also be understood from the entirety of the specification and the claims filed herein.

Example 1. A method including: receiving reflected radar signals with a millimeter-wave radar; generating a displacement signal indicative of a displacement of a target based on the reflected radar signals; filtering the displacement signal using a bandpass filter to generate a filtered displacement signal; determining a first rate indicative of a heartbeat rate of the target based on the filtered displacement signal; tracking a second rate indicative of the heartbeat rate of the target with a track using a Kalman filter; updating the track based on the first rate; and updating a setting of the bandpass filter based on the updated track.

Example 2. The method of example 1, further including determining a gating region using a gating function, where updating the track includes updating the track when the first rate is inside the gating region, and where updating the setting of the bandpass filter includes narrowing a pass-band of the bandpass filter based on the updated track.

Example 3. The method of one of examples 1 or 2, where the gating function is an ellipsoidal gating function.

Example 4. The method of one of examples 1 to 3, further including: incrementing a counter when the first rate is outside the gating region; and increasing the pass-band of the bandpass filter when the counter reaches a count of M, where M is a positive integer greater than 1.

Example 5. The method of one of examples 1 to 4, where increasing the pass-band of the bandpass filter includes increasing the pass-band based on the track.

Example 6. The method of one of examples 1 to 5, where updating the setting of the bandpass filter based on the updated track includes adjusting a lower cutoff frequency of the bandpass filter or a higher cutoff frequency the bandpass filter based on an uncertainty value associated with the updated track.

Example 7. The method of one of examples 1 to 6, where updating the setting of the bandpass filter based on the updated track includes adjusting a center frequency of the bandpass filter.

Example 8. The method of one of examples 1 to 7, where the bandpass filter has an initial pass-band from 0.7 Hz to 3 Hz.

Example 9. The method of one of examples 1 to 8, where generating the displacement signal includes: generating range data based on the reflected radar signals; performing target detection based on the range data to detect the target; and generating the displacement signal based on in-phase (I) and quadrature (Q) signals associated with the detected target.

Example 10. The method of one of examples 1 to 9, where the range data corresponds to a range-Doppler image or a range cross-range image.

Example 11. The method of one of examples 1 to 10, where performing target detection includes determining a target range bin, and where generating the displacement signal includes generating the displacement signal when a standard deviation in the target range bin is below a predetermined threshold.

Example 12. The method of one of examples 1 to 11, where estimating the first rate includes counting peaks in the filtered displacement signal.

Example 13. The method of one of examples 1 to 12, where the target is a human target.

Example 14. The method of one of examples 1 to 13, further including transmitting radar signals with the millimeter-wave radar, where the transmitted radar signals include linear chirps.

Example 15. A device including: a millimeter-wave radar configured to transmit chirps and receive reflected chirps; and a processor configured to: generate a displacement signal indicative of a displacement of a target based on the reflected chirps, filter the displacement signal using a bandpass filter to generate a filtered displacement signal, determine a first rate indicative of a heartbeat rate of the target based on the filtered displacement signal, track a second rate indicative of the heartbeat rate of the target with a track using a Kalman filter, update the track based on the first rate, and update a setting of the bandpass filter based on the updated track.

Example 16. The device of example 15, where the millimeter-wave radar includes the processor.

Example 17. A method for tracking a vital rate indicative of a heartbeat rate of a human target using a track of a Kalman filter, the method including: receiving reflected radar signals; generating a displacement signal indicative of a displacement of a target based on the reflected radar signals; filtering the displacement signal using a bandpass filter to generate a filtered displacement signal; generating a heartbeat rate estimate based on the filtered displacement signal; determining a heartbeat rate prediction and an uncertainty prediction based on the track; determining whether the heartbeat rate estimate is an outlier based on the uncertainty prediction; and when the heartbeat rate estimate is determined to be not an outlier, updating the track based on the heartbeat rate estimate; and updating a setting of the bandpass filter based on the updated track.

Example 18. The method of example 17, where determining whether the heartbeat rate estimate is an outlier includes: determining a gating region using an ellipsoidal gating function based on the uncertainty prediction; determining that the heartbeat rate estimate is an outlier when a result of the ellipsoidal gating function is higher than a predetermined threshold; and determining that the heartbeat rate estimate is not an outlier when the result of the ellipsoidal gating function is lower than the predetermined threshold.

Example 19. The method of one of examples 17 or 18, where updating the setting the bandpass filter includes adjusting a lower cutoff frequency of the bandpass filter or a higher cutoff frequency the bandpass filter based on the uncertainty prediction.

Example 20. The method of one of examples 17 to 19, further including, when the heartbeat rate estimate is determined to be an outlier: incrementing a counter; and increasing a pass-band of the bandpass filter when the counter reaches a count of M, where M is a positive integer greater than 1.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method comprising:
   receiving reflected radar signals with a millimeter-wave radar;
   generating a displacement signal indicative of a displacement of a target based on the reflected radar signals;
   filtering the displacement signal using a bandpass filter to generate a filtered displacement signal;
   determining a first rate indicative of a heartbeat rate of the target based on the filtered displacement signal;
   tracking a second rate indicative of the heartbeat rate of the target with a track using a Kalman filter;
   determining a gating region using a gating function;
   updating the track when the first rate is inside the gating region; and
   updating a setting of the bandpass filter to narrow a pass-band of the bandpass filter based on the updated track.

2. The method of claim 1, wherein the displacement signal is a time-domain signal.

3. The method of claim 1, wherein the gating function is an ellipsoidal gating function.

4. The method of claim 1, further comprising:
   incrementing a counter when the first rate is outside the gating region; and
   increasing the pass-band of the bandpass filter when the counter reaches a count of M, wherein M is a positive integer greater than 1.

5. The method of claim 4, wherein increasing the pass-band of the bandpass filter comprises increasing the pass-band based on the track.

6. The method of claim 1, wherein updating the setting of the bandpass filter based on the updated track comprises adjusting a lower cutoff frequency of the bandpass filter or a higher cutoff frequency of the bandpass filter based on an uncertainty value associated with the updated track.

7. The method of claim 1, wherein updating the setting of the bandpass filter based on the updated track comprises adjusting a center frequency of the bandpass filter.

8. The method of claim 1, wherein the bandpass filter has an initial pass-band from 0.7 Hz to 3 Hz.

9. The method of claim 1, wherein generating the displacement signal comprises:
   generating range data based on the reflected radar signals;
   performing target detection based on the range data to detect the target; and
   generating the displacement signal based on in-phase (I) and quadrature (Q) signals associated with the detected target.

10. The method of claim 9, wherein the range data corresponds to a range-Doppler image or a range cross-range image.

11. The method of claim 9, wherein performing target detection comprises determining a target range bin, and wherein generating the displacement signal comprises generating the displacement signal when a standard deviation in the target range bin is below a predetermined threshold.

12. The method of claim 1, wherein estimating the first rate comprises counting peaks in the filtered displacement signal.

13. The method of claim 1, wherein the target is a human target.

14. The method of claim 1, further comprising transmitting radar signals with the millimeter-wave radar, wherein the transmitted radar signals comprise linear chirps.

15. A device comprising:
   a millimeter-wave radar configured to transmit chirps and receive reflected chirps; and
   a processor configured to:
      generate a displacement signal indicative of a displacement of a target based on the reflected chirps,
      filter the displacement signal using a bandpass filter to generate a filtered displacement signal,
      determine a first rate indicative of a heartbeat rate of the target based on the filtered displacement signal,
      track a second rate indicative of the heartbeat rate of the target with a track using a Kalman filter,
      determine a gating region using a gating function,
      update the track when the first rate is inside the gating region, and
      update a setting of the bandpass filter to narrow a pass-band of the bandpass filter based on the updated track.

16. The device of claim 15, wherein the millimeter-wave radar comprises the processor.

17. The device of claim 15, wherein updating the setting of the bandpass filter based on the updated track comprises adjusting a lower cutoff frequency of the bandpass filter or a higher cutoff frequency of the bandpass filter based on an uncertainty value associated with the updated track.

18. A method for tracking a vital rate indicative of a heartbeat rate of a human target using a track of a Kalman filter, the method comprising:
   receiving reflected radar signals;
   generating a displacement signal indicative of a displacement of a target based on the reflected radar signals;
   filtering the displacement signal using a bandpass filter to generate a filtered displacement signal;
   generating a heartbeat rate estimate based on the filtered displacement signal;
   determining a heartbeat rate prediction and an uncertainty prediction based on the track;
   determining whether the heartbeat rate estimate is an outlier based on the uncertainty prediction; and
   when the heartbeat rate estimate is determined to be not an outlier,
      updating the track based on the heartbeat rate estimate, and adjusting a lower cutoff frequency of the bandpass filter or a higher cutoff frequency the bandpass filter based on the uncertainty prediction.

19. A method for tracking a vital rate indicative of a heartbeat rate of a human target using a track of a Kalman filter, the method comprising:
receiving reflected radar signals;
generating a displacement signal indicative of a displacement of a target based on the reflected radar signals;
filtering the displacement signal using a bandpass filter to generate a filtered displacement signal;
generating a heartbeat rate estimate based on the filtered displacement signal;
determining a heartbeat rate prediction and an uncertainty prediction based on the track:
determining a gating region using an ellipsoidal gating function based on the uncertainty prediction;
determining that the heartbeat rate estimate is an outlier when a result of the ellipsoidal gating function is higher than a predetermined threshold;
determining that the heartbeat rate estimate is not an outlier when the result of the ellipsoidal gating function is lower than the predetermined threshold; and
when the heartbeat rate estimate is determined to be not an outlier,
updating the track based on the heartbeat rate estimate, and
updating a setting of the bandpass filter based on the updated track.

20. A method for tracking a vital rate indicative of a heartbeat rate of a human target using a track of a Kalman filter, the method comprising:
receiving reflected radar signals;
generating a displacement signal indicative of a displacement of a target based on the reflected radar signals;
filtering the displacement signal using a bandpass filter to generate a filtered displacement signal;
generating a heartbeat rate estimate based on the filtered displacement signal;
determining a heartbeat rate prediction and an uncertainty prediction based on the track;
determining whether the heartbeat rate estimate is an outlier based on the uncertainty prediction;
when the heartbeat rate estimate is determined to be not an outlier,
updating the track based on the heartbeat rate estimate, and
updating a setting of the bandpass filter based on the updated track; and
when the heartbeat rate estimate is determined to be an outlier:
incrementing a counter, and
increasing a pass-band of the bandpass filter when the counter reaches a count of M, wherein M is a positive integer greater than 1.

* * * * *